United States Patent [19]

Chodorow

[11] Patent Number: 5,692,531
[45] Date of Patent: Dec. 2, 1997

[54] DUAL STRAND DENTAL FLOSSER AND METHOD OF MANUFACTURING SAME

[75] Inventor: Ingram S. Chodorow, Upper Saddle River, N.J.

[73] Assignee: Placontrol Corporation, Montvale, N.J.

[21] Appl. No.: 324,479

[22] Filed: Oct. 17, 1994

Related U.S. Application Data

[63] Continuation-in-part of Ser. No. 114,424, Aug. 30, 1993, Pat. No. 5,538,023.

[51] Int. Cl.$^6$ ........................................... A61C 15/00
[52] U.S. Cl. ............................................. 132/323
[58] Field of Search .......................... 132/321, 323, 132/324, 325, 326, 327, 322

[56] References Cited

U.S. PATENT DOCUMENTS

| | | | |
|---|---|---|---|
| D. 244,376 | 5/1977 | Chodorow | D28/64 |
| D. 250,214 | 11/1978 | Chodorow | D28/64 |
| D. 251,074 | 2/1979 | Schiff | D28/64 |
| D. 251,075 | 2/1979 | Schiff | D28/64 |
| D. 301,071 | 5/1989 | Franchi | D28/64 |
| D. 312,894 | 12/1990 | Schroder-Jorgensen | D28/64 |
| 413,001 | 10/1889 | Walsh | 132/323 |
| 1,415,762 | 5/1922 | Bailey | 132/323 |
| 2,443,415 | 6/1948 | Buscarino | 132/323 |
| 2,702,555 | 2/1955 | DeMar | 132/323 |
| 2,811,162 | 10/1957 | Brody | 132/323 |
| 3,693,594 | 9/1972 | Ciccarelli | 132/323 |
| 3,858,594 | 1/1975 | Ensminger | |
| 4,006,750 | 2/1977 | Chodorow | 132/323 |
| 4,016,892 | 4/1977 | Chodorow | 132/91 |
| 4,192,330 | 3/1980 | Johnson | 132/323 |
| 4,522,216 | 6/1985 | Bunker | 132/323 |
| 4,807,651 | 2/1989 | Naydich | 132/323 |
| 4,832,062 | 5/1989 | Grollimund et al. | 132/324 |
| 4,982,752 | 1/1991 | Rodriguez | 132/324 |
| 5,033,488 | 7/1991 | Curtis et al. | 132/321 |
| 5,086,792 | 2/1992 | Chodorow | 132/323 |
| 5,113,880 | 5/1992 | Honda et al. | 132/321 |
| 5,123,432 | 6/1992 | Wyss | 132/323 |

FOREIGN PATENT DOCUMENTS

| | | | |
|---|---|---|---|
| 3920256 | 2/1960 | Germany | 132/323 |
| 1095460 | 12/1960 | Germany | 132/323 |

*Primary Examiner*—Cary E. O'Conner
*Attorney, Agent, or Firm*—Ostrolenk, Faber, Gerb & Soffen, L.L.P.

[57] ABSTRACT

A dental floss holder comprising: a body part, first and second spaced apart arms extending from the body part, a first strand of dental floss extending generally axially between the arms, the strand having opposite ends secured to the arms, and a second strand of dental floss extending generally axially between the arms and situated generally parallel to and laterally displaced from the first strand.

22 Claims, 11 Drawing Sheets

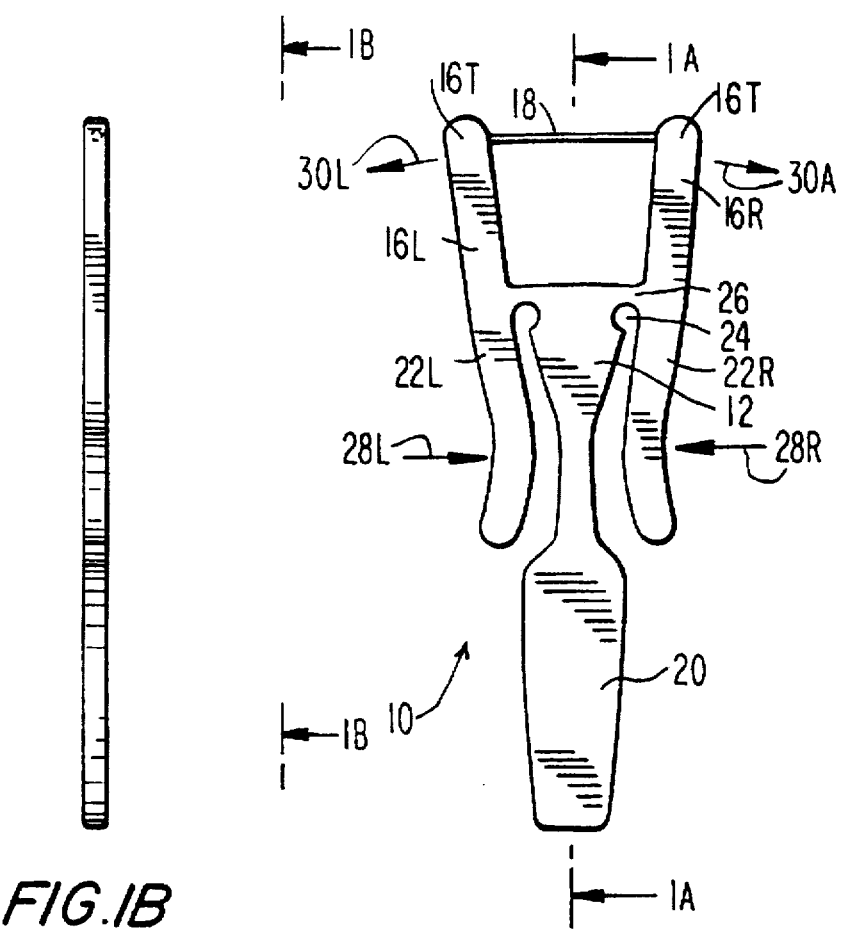
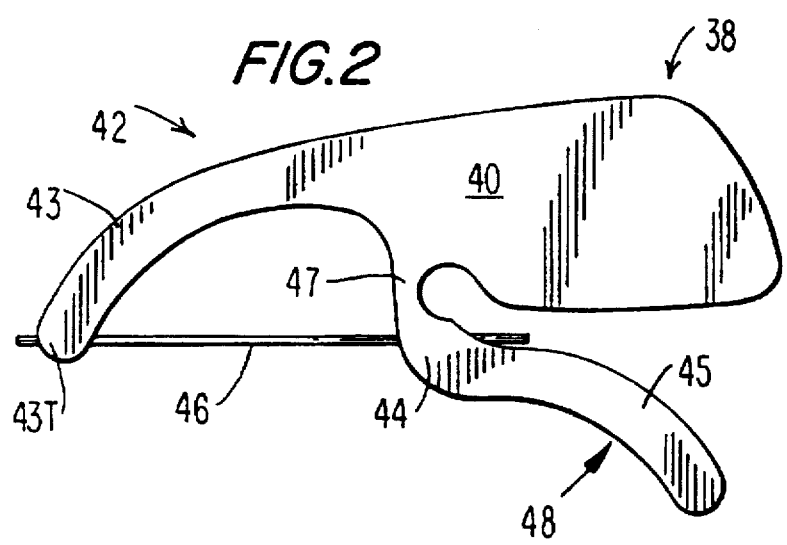

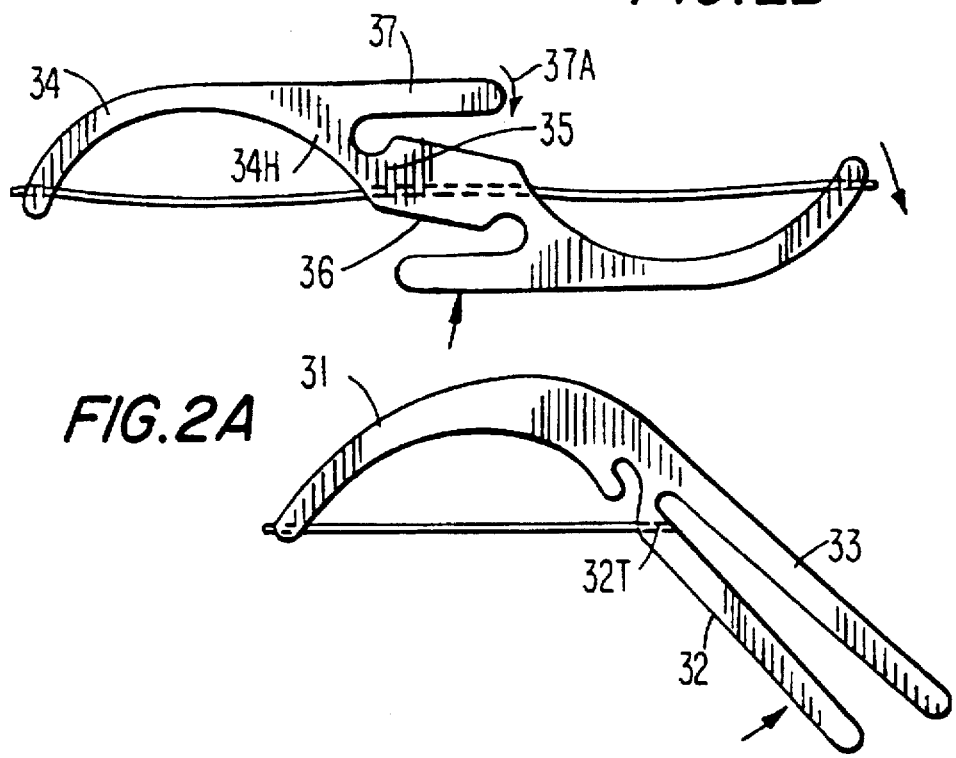
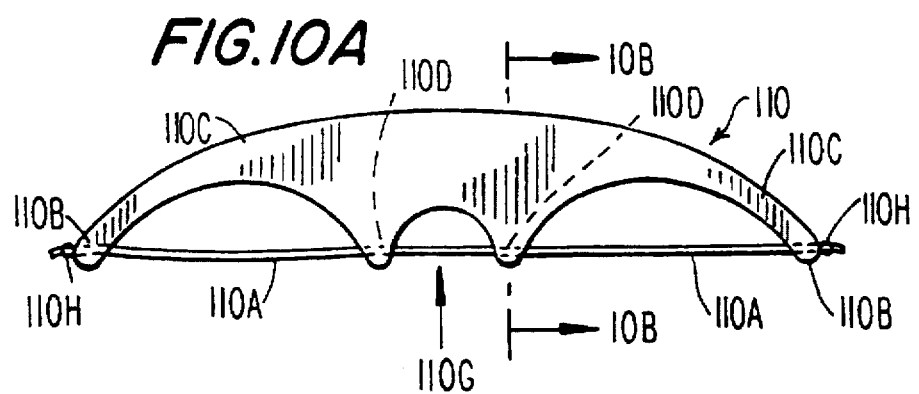
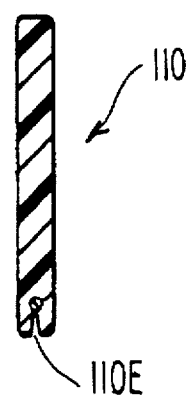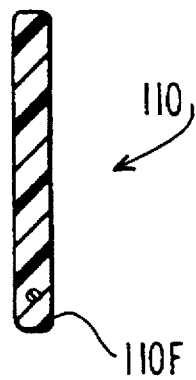

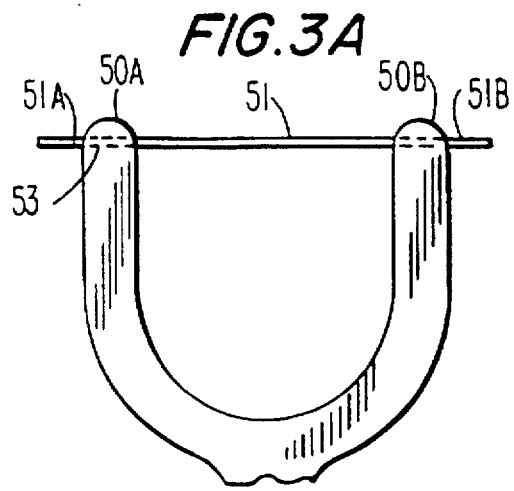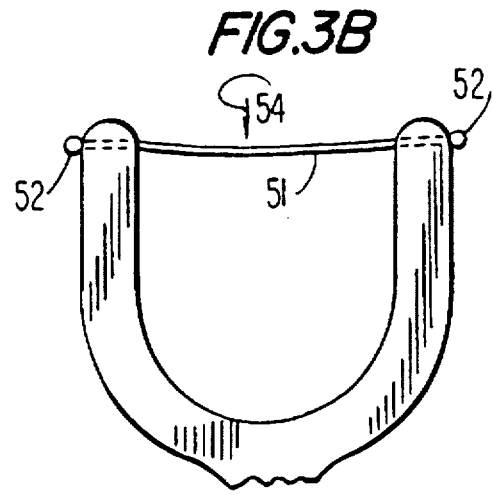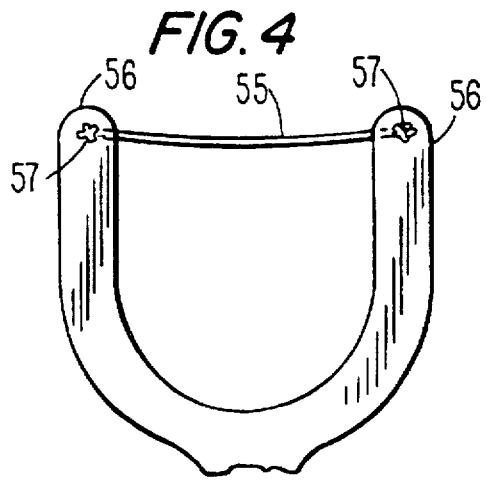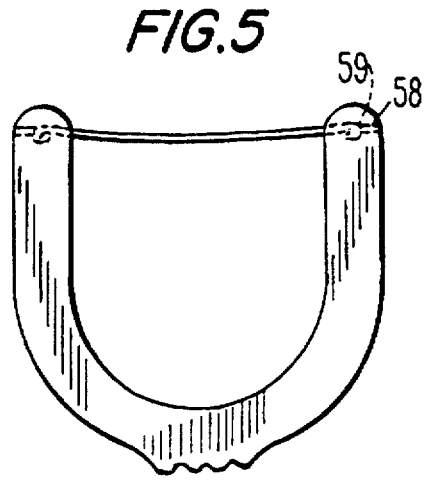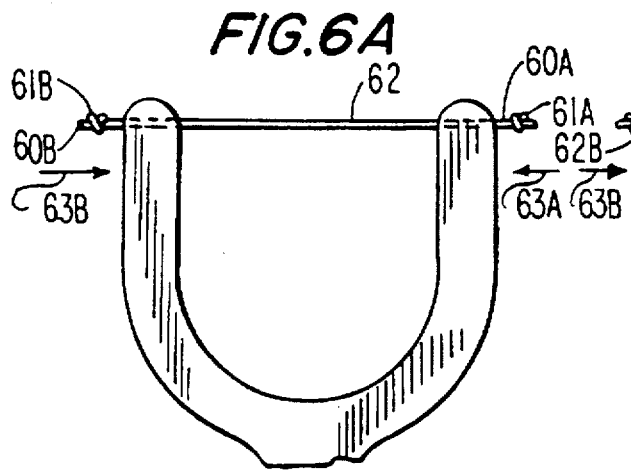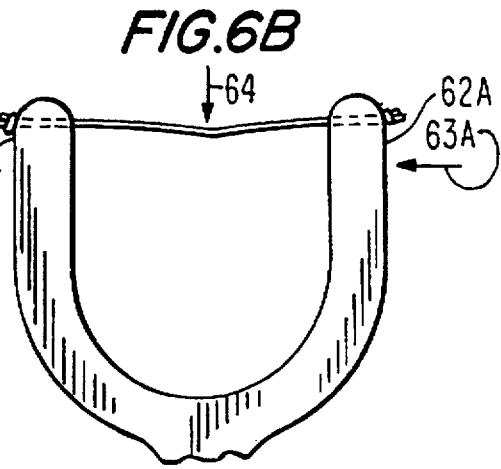

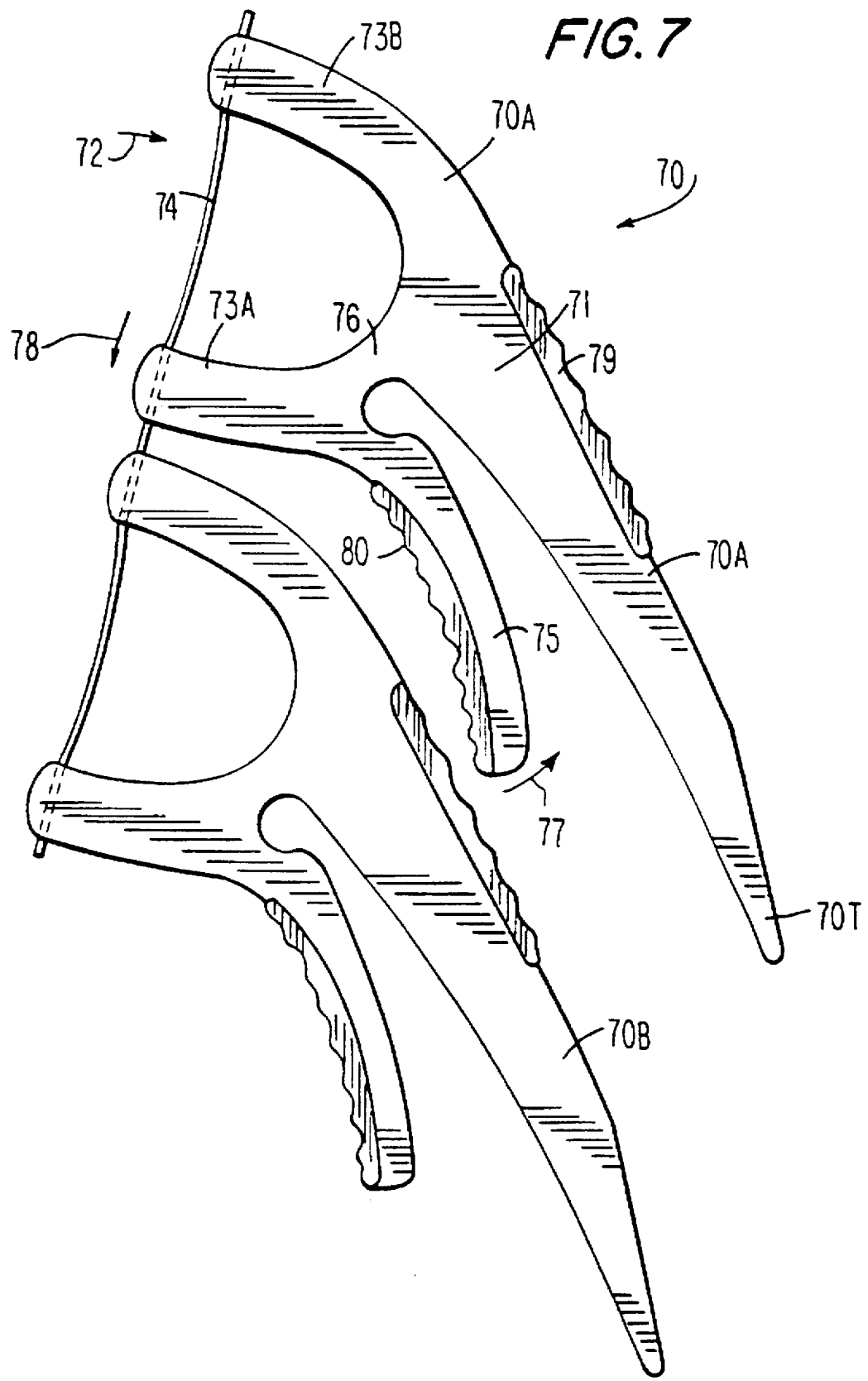

FIG.8A
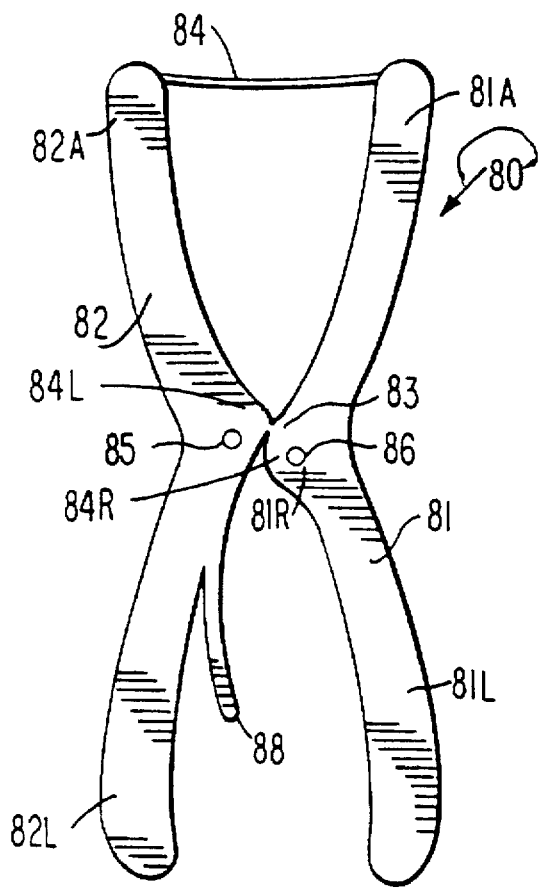
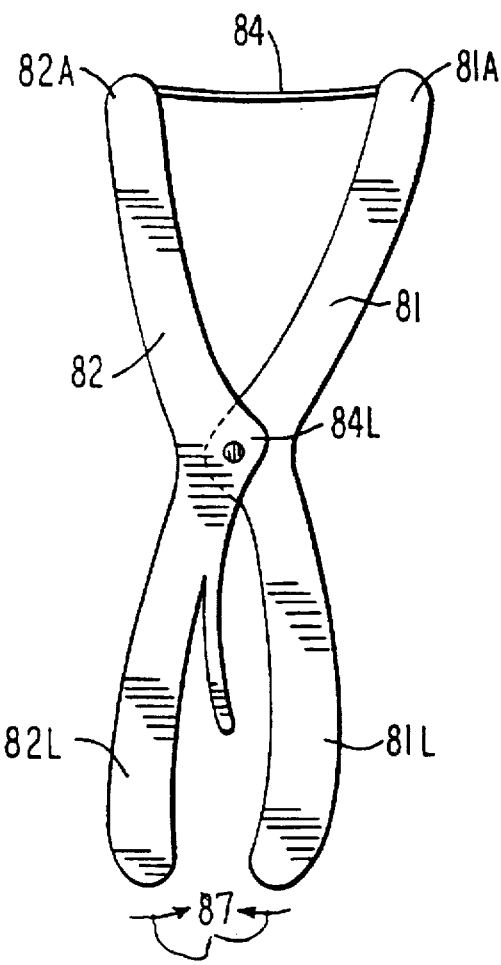
FIG.8B

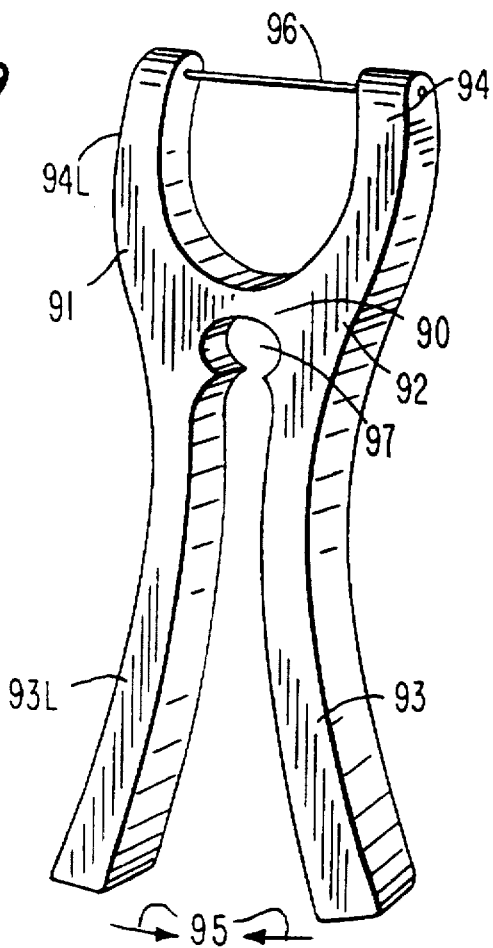
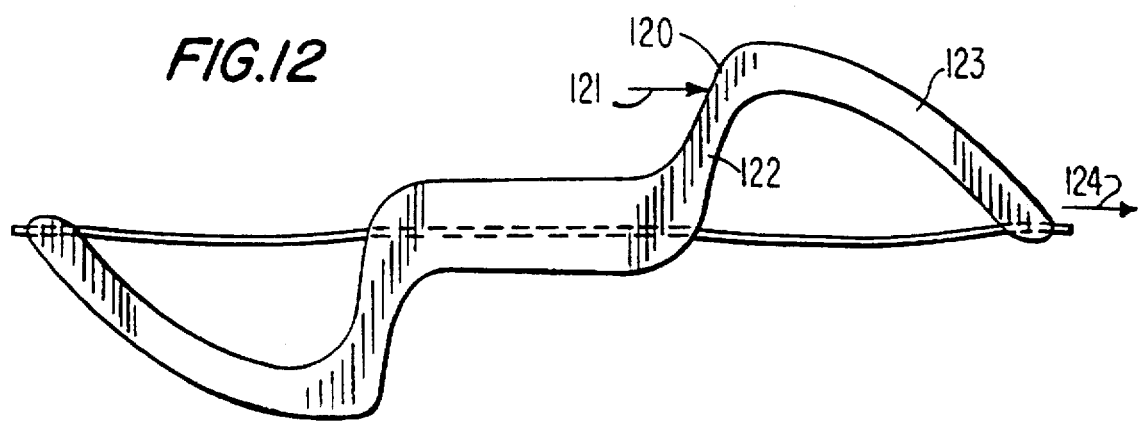

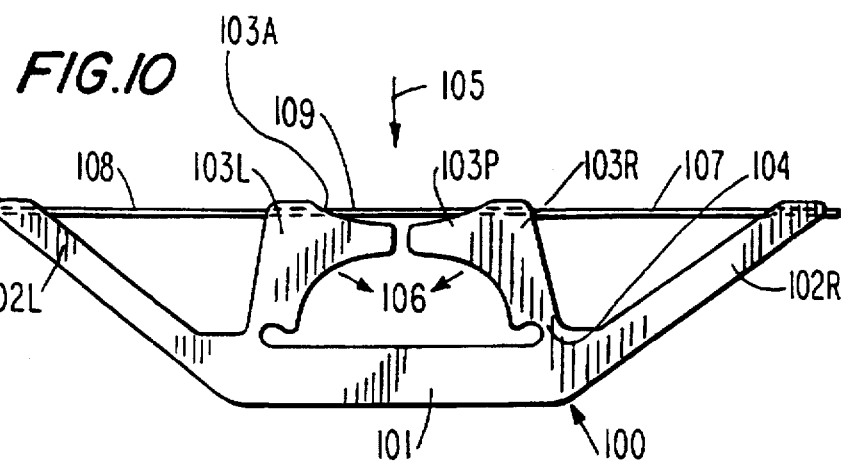
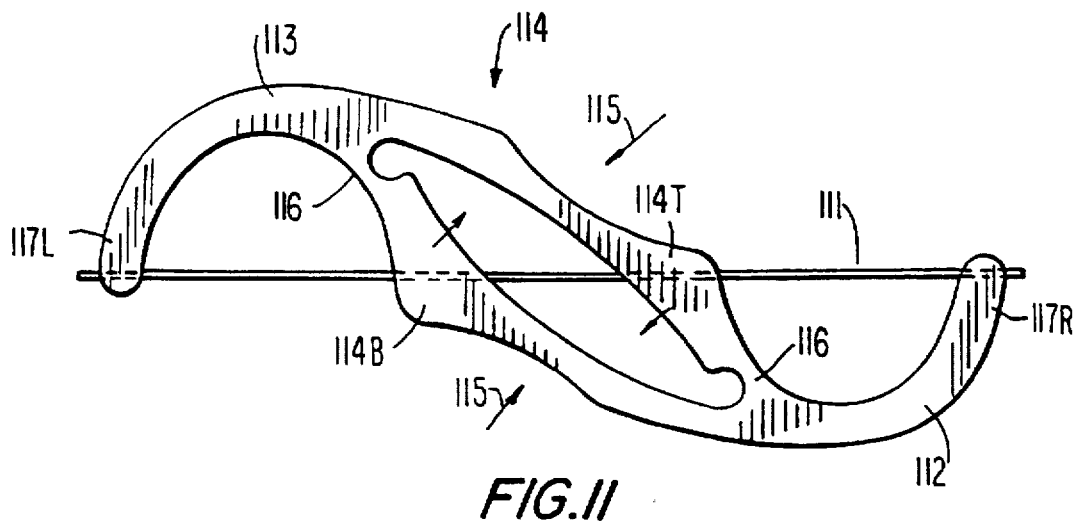

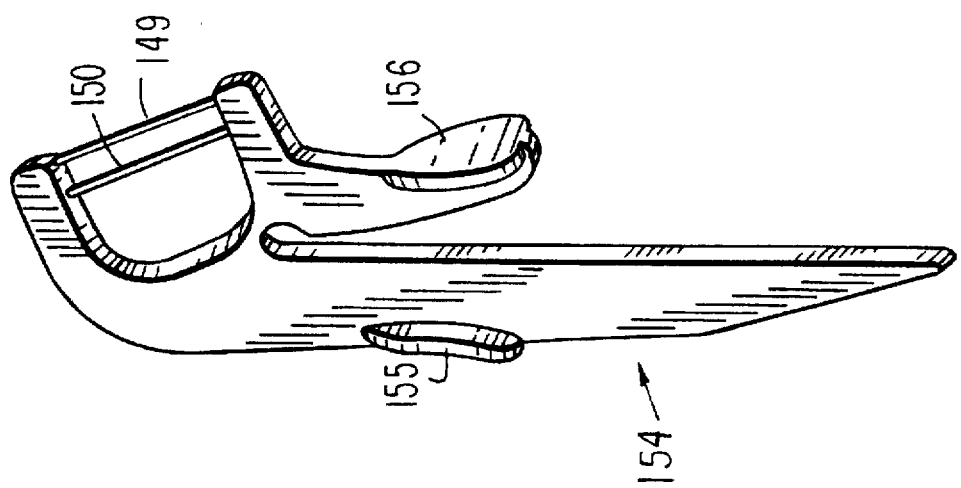
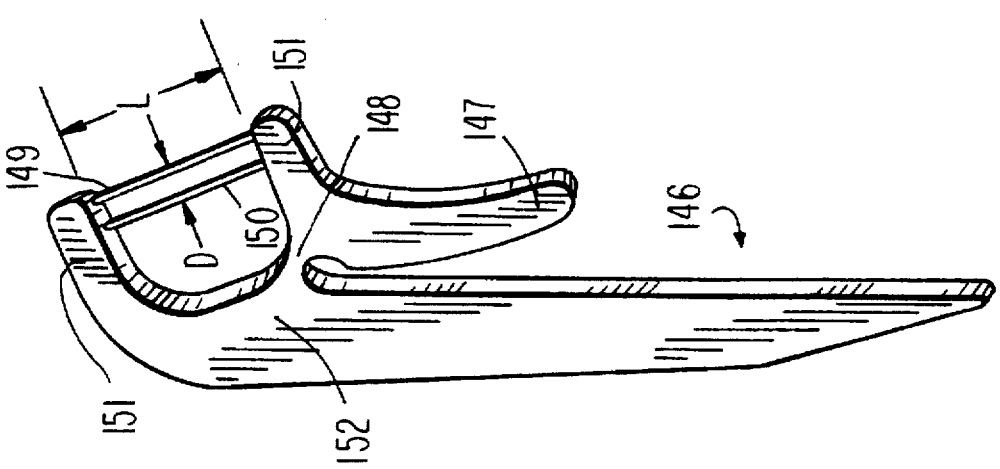
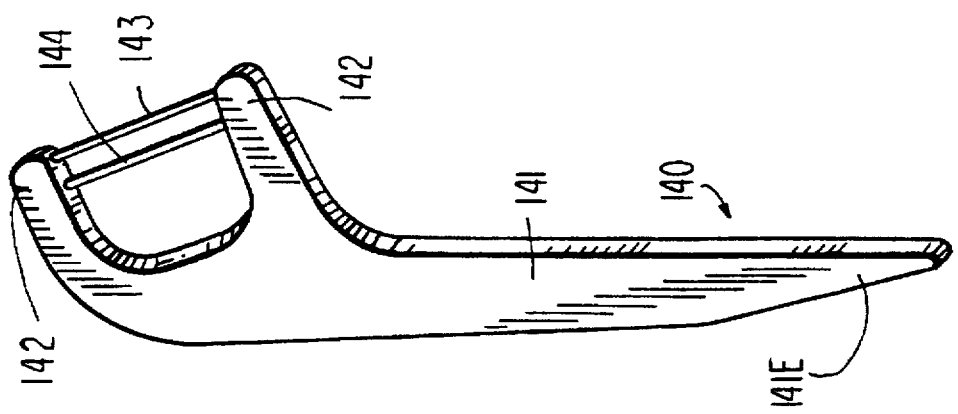

5,692,531

DUAL STRAND DENTAL FLOSSER AND METHOD OF MANUFACTURING SAME

This application is a continuation-in-part of the application Ser. No. 08/114,424, filed Aug. 30, 1993, now U.S. Pat. No. 5,538,023.

BACKGROUND OF THE INVENTION

1. Field of the Invention

This invention is in the field of disposable dental floss holders and particularly injection molded devices, each formed integrally as a handle plus a bow across which a strand of dental floss is spanned, and in the field of manufacturing dental floss holders.

2. Related Inventions

This invention is related to disclosures in the following U.S. patents:

| U.S. Pat. No. | Inventor | Date |
| --- | --- | --- |
| 4,006,750 | I. S. Chodorow | 02/08/77 |
| 4,016,892 | I. S. Chodorow | 02/08/77 |
| D 244,376 | I. S. Chodorow | 05/77 |
| D 250,214 | | |
| D 251,075 | N. Schiff | 02/13/79 |
| D 251,074 | N. Schiff | 02/13/79 |
| D 301,071 | R. Franchi | 05/09/89 |
| D 312,894 | J. Scroder-Jorgensen | 12/11/90 |
| 3,858,594 | G. Ensminger | 01/07/75 |
| 5,086,792 | I. S. Chodorow | 02/11/92 |

3. Background and Prior Art

This invention is in the field of devices for personal and professional dental care, particularly for removing plaque from the teeth surfaces and food particles from between teeth.

For many years teeth have been cleaned primarily by manual or power-driven brushing, and the spaces between teeth have been cleaned by a variety of methods including brushing, machine-driven jets of water, toothpicks, and the like, and by flossing with the commonly available nylon dental floss and dental tape or similar thread or even rubber bands.

Until recently the most generally accepted objective in cleaning teeth was to remove food particles and chemicals, particularly sweets from tooth surfaces. However, now it has been established and is being taught by a growing number of dentists, orthodontists and periodontists, that the chief cause of caries (dental cavities) and a principal cause of periodontal (gum and root) disease is a bacterial plaque formation that develops on tooth surfaces. When removed, new plaque can reform in less than 24 hours. The causes of plaque development are not fully appreciated; however, a person's normal body chemistry independent of his particular diet, can be a contributing factor.

Plaque is the name given to a bacterial substance that begins as an invisible film of micro-organisms, and with saliva and foods, particularly sugars, forms a soft sticky white film on the surfaces of teeth and between teeth. If plaque is not removed daily it can develop and harden into a firmly attached substance called calculus or tartar which may cause gums to redden and swell in a condition known as gingivitis. This disease is often characterized by receding gums which causes the creation of small pockets around the teeth which trap food particles and bacteria. These pockets can enlarge if the gums become further inflamed or infected causing the bone supporting the teeth to become infected and destroyed. The weakened tissue is infection-prone and once so injured the gums cannot protect the underlying bone from the spread of this disease. Additionally, bacterial plaque produces noxious chemicals which cause cavities and irritate the gums. This is the manner in which teeth become loosened and ultimately lost, the latter stages here-described being periodontal disease.

Of the methods mentioned above for cleaning teeth, brushing is not effective to remove plaque from interdental tooth surfaces between the teeth. Water jets are not sufficiently abrasive to achieve plaque removal, though they may remove food particles very well. Also, toothpicks are too thick and cumbersome to probe and scrape between two closely adjacent surfaces. This leaves only dental floss, typically a strand of multi-filamented nylon that is moved in a reciprocating action into the crack or space between the sides of two teeth. The unwaxed version of dental floss is less smooth and thus more abrasive and more effective in scraping plaque off the tooth enamel surfaces in question. However, the user of any floss has the problem of maneuvering it—while under certain tension, down between each pair of teeth, including the rear-most teeth. Positioning floss is inconvenient in most teeth locations, quite difficult in many, and almost impossible in others. The procedure generally requires: winding opposite ends of a strand around the middle finger of each hand respectively, then over the two index fingers of both hands which are placed into the mouth, attempting to position the span of floss between the fingers in the desired location, and finally reciprocating the floss between teeth while also moving it vertically along the tooth from tip to gum. The floss is maneuvered preferably just under the edge of the gum, held firmly against and wrapped partially around the proximal surface of the tooth and pulled over its surface toward the chewing edge.

It is known from surveys that most people, even including those who take seriously the matter of dental care and brushing regularly, do not use floss daily because the technique for use as described above is so tedious. For a number of years there have been attempts to render flossing less tedious and also to render it more effective by the development of holders onto which floss is attached. Most holders have two arms across which the floss is strung; however, secondary complications described below with the holders themselves have resulted in general non-use, and thus there has been no remedy to the original problem of promoting the regular use of floss held by hand.

One basic problem with the holders is that because they are non-disposable, they are too large. Floss stretches on them, eventually frays, and breaks during use. Whether the floss holds up for five, twenty or more teeth depends upon the tightness of the interdental spaces and the abrasion the floss incurs. By the original manual operation before floss holders, the floss user merely pulled the exposed end of floss from a spool, cut off a segment and then wound the cut segment on the fingers. With certain floss holder devices the user must, for each flossing operation, obtain a length of floss, thread or carefully position it about a floss holder, pull on some part of the floss until it is in tension, and finally secure it under tension to the holder. Whether a floss supply is provided on a spool in the holder handle according to one device, or provided from a separate spool from which segments of floss are cut as needed, the remaining threading and tensioning procedure is still an inconvenient burden.

From these manually strung or manually loaded flossing devices there developed pre-strung disposable flossers where a strand of floss of length to span the bow or spaced arms of the flosser had its ends secured to the arms in situ, namely at the same time the flosser handle and arms were injection molded. These devices have gained wide popularity and sales because they are convenient to use and to carry, and because they can be mass produced and sold at very low per unit cost.

Samples of prior art flossers of the type with an injection molded handle and floss pre-strung at the time of molding, and disclosures of known manufacturing methods may be seen in U.S. Pat. Nos. 4,006,750, 4,016,892, 5,086,792 and in the other patents cited above which are hereby incorporated herein by reference. These and similar devices, regardless of the geometric configuration of the handle, have certain useful features in common and certain troublesome features in common. On the positive side are the light weight and inexpensive holders, each with a bow portion formed by spaced arms and a segment of floss spanning the bow. Some configurations, i.e. with floss parallel to the handle, may be more convenient than others for particular users.

On the negative side, applying to all prior art disposable flossers with a permanently prestrung bow portion, are the following points. A typical user of a dental floss holder (flosser) would like to use a single flosser or as few flossers as possible to clean between all the teeth in his/her mouth. Thus, the same floss segment spanning the bow of the flosser will be inserted repeatedly between different adjacent teeth. If the floss is the multifilament type and if at least some of the teeth are closely or tightly adjacent, the floss in the flosser becomes stretched and/or frayed and may even break. Monofilament floss tends less to stretch, fray or break; however, it is less abrasive than multifilament floss, less effective in removing plaque, and thus less desirable for many floss users.

Tensioning of the floss occurs each time the floss strand is urged to pass into the interspace between two closely or tightly adjacent teeth. After one or more tensioning uses of a strand of floss in a holder it will stretch and then have slack and no longer be taut and linear between the arms or ends of the bow. Consequently, the next time the flosser with slack floss is used to penetrate the interspace between two teeth the floss takes a deep generally V-shaped configuration as penetration of the interspace is begun. This leads to two undesirable consequences. First, since the floss is not taut the bow must be moved further toward the gums than if the floss were taut. When the floss pops through the interspace the bow ends may be positioned below the gum line, so the floss will pop through trying to reach a neutral condition and strike the gum, which is highly undesirable as it can cut, bruise or otherwise harm the gum.

Another reason why some prior art pre-strung flossers develop slack floss is because one or both floss ends slip slightly out of an arm of the bow during tensioning as the flosser is used. Slippage occurs when the floss is not well bonded to the holder which may occur because the plastics of the floss and handle are incompatible or because the floss and the injection molded plastic are not heated and cooled uniformly or at least not at appropriate respective temperatures and time periods for secure bonding together.

In conclusion, floss often stretches and subsequent attempts to use a flosser with stretched floss present difficulties or undesirable situations for the user. If the floss ends are well-anchored in the bow arms, stretching still occurs. If the floss ends are not well anchored the floss slips and slack results. Either way, after a few penetrations of interspaces many flossers have lost their tension of the floss.

In the new invention we have identified a problem and discovered a solution in the form of a new device and a new method of manufacturing these devices, as set forth below.

SUMMARY OF THE INVENTION

According to the present invention it was discovered that the greater the tension on floss prior to and during insertion and removal from between two teeth, the easier it is to insert and remove the floss and overcome the friction created by the pressure two teeth may exert against each other. However, when the floss has become inserted into the interspace between two teeth and is being used to clean plaque off of tooth surfaces or to remove food particles from between teeth, it was further discovered that the floss preferably should not be under great tension so that is can be partially wrapped around a portion of the tooth.

As discussed in the description of prior art above, floss in holders becomes slack either from stretching after one or more uses, or from slipping within an arm, or from warping or shrinking of the arm(s) toward each other at the conclusion of the molding process.

The new invention is a floss holder designed to be disposable, i.e. to be discarded after the user has completed whatever degree of flossing he or she requires. The new invention further provides one or more bows of floss in a single holder, the floss having ends permanently embedded in the arms of the bow, and unique means within the holder that enable the user to apply temporary force on a portion of the holder which causes the distance between two opposing portions of the bow that hold the floss to increase thereby increasing the tension on the floss and reducing slack in the strand of floss. The new invention further provides a method of making these yoke-like holders with the floss attached, in a single manufacturing step which greatly reduces cost.

In one embodiment of the new invention the user applies slight pressure to a tensioning arm by pushing or pulling it against the handle. In that the tensioning arm is integral with one of the sections of the bow in which floss is captured, that section of the bow will move in sympathy with the tensioning arm thereby causing the tension on the floss to increase. The user is therefore able to exert considerable control over the tension of the floss with the use of only one hand. This makes flossing very fast, easy, effective and economical.

According to the present invention it was discovered that regardless of the amount of tension of the floss in the holder at the time of manufacture, during insertion of the floss and later during sawing action, the floss stretches such that the point of teeth-floss contact is outside the line extending between the two tips of the holder arms, with the floss thus formed into a wide angle or curve. The floss once inserted is partially wrapped around and conformed to curved surfaces of a tooth to scrape a greater amount of surface, in contrast to a strand of floss in straight line tension that tends to retain its straight-line- or linear configuration, minimizing its degree of contact with curved tooth surfaces. However, for the next penetration between two other teeth the slack floss is more difficult to insert than when it was taut earlier.

Where two teeth have their adjacent surfaces very close together forming a tight interdental space, it is often very difficult to maneuver and force a strand of floss down between these teeth to the gum and then out again. For this type of situation it can be helpful to use a different embodiment of the new invention, wherein the floss is placed in tension during manufacture, such that the floss "in a straight-line or linear configuration" is tensioned between the holder's arms, as contrasted with floss in tension only after being formed into a V-shaped configuration while engaging the teeth. With this alternate embodiment the floss is taut in all positions and orientations of the holder, which is helpful to some users, especially where tight spaces are prevalent. In the embodiment where tension of the floss is established during manufacture, this added tension helps compensate for any tendency for slack to develop where shrinkage of the plastic occurs during solidification. In fact the arms can be designed so that if shrinkage is unavoidable, it will occur more severely in selected areas to cause the arms to shrink or warp away from each other and thus stretch the capture floss between said arms.

The new invention is a floss holder device designed to be disposable, i.e. to be thrown away after a user "flosses" some or all of his teeth. The new invention further provides a method of making these yoke-like holders with the floss attached in a single manufacturing step which greatly reduces cost.

According to this method, floss is positioned in a multi-cavity mold, prior to injection molding of a suitable plastic into the cavities. The resulting product is complete and ready for use with no requirement of an additional step of threading, tensioning, or securing floss; also it can be considerably less expensive than all other known holders which are designed to have the floss attached separately and furthermore tensioned.

Another feature of this invention is the intentional heating of the cut end of the floss to form a bead where the floss exits the arms, i.e. heating the floss either simultaneous with the cutting or as a separate step following cutting.

A further embodiment of this invention is a dental flosser with two or more lines of floss captured between the arms of the holder. This double or more lines of floss configuration is applicable to the tensioning flosser described above and to more traditional flossers having no tensioning capability. Advantages of this double line flosser include increased cleaning action by the multiple strands of floss and providing back-up floss in case one strand frays or breaks. In some embodiments a finer denier would be used than in a typical single line flosser, which would facilitate passage between teeth.

A still further embodiment comprises a flat holder having essentially uniform thickness, except for thicker areas on one or more outer edges where the user's fingers grasp or engage the holder. Such thickened areas are particularly desirable on tensioning floss holders where the user's fingers press the edges.

In addition to designing a dental flosser for its use function, another consideration is the packaging of the product in multiples that will allow compact and attractive stacking. Where the holder has thicker outer edges, stacking is still possible with relatively reduced space by providing appropriately located recesses or apertures in the surface of one holder to receive the thicker protruding edges of the next adjacent holder. In a stack of these type holders the position of each would be slightly displaced from the one above and below which could produce a "shingled" appearance. With this arrangement the flat central body parts of each holder lie essentially surface-to-surface, occupying the same total height as a stack of holders that do not have thickened grasping edges. The off-set, staggered or shingled aspect causes a wider "footprint" or side-to-side dimension, but the stack is still substantially compact as is useful for certain commercial packaging such as blisterpaks.

The embodiments of the invention summarized above will be described in greater detail below in conjunction with the drawings appended hereto.

BRIEF DESCRIPTION OF THE DRAWINGS

FIG. 1 is a top plan view of a first embodiment of the new invention showing a dental floss holder.

FIG. 1A is a sectional view taken along line A—A in FIG. 1.

FIG. 1B is a left side elevation view of FIG. 1.

FIG. 2 is a top plan view of a second embodiment of the invention.

FIG. 2A is a top plan view of another embodiment as a variation of the device of FIG. 2

FIG. 2B is a top plan view of another embodiment as a further variation of the device of FIG. 2.

FIG. 3A is a fragmentary top plan view of a third embodiment of the invention showing the floss spanning a pair of arms of a floss holder or bow with terminal ends of the floss extending outward of the arms at a preliminary stage of manufacture.

FIG. 3B is a view similar to FIG. 3A showing that the projecting ends of the floss having been heated to form beads at the outer surface of the arms.

FIG. 4 is a fragmentary plan view of a fourth embodiment with the terminal end of the floss formed into a knot and embedded in the arms.

FIG. 5 is a fragmentary top plan view of a fifth embodiment with the terminal ends of the floss formed into loops which are embedded in the arms.

FIG. 6A is fragmentary top plan view of a sixth embodiment where the terminal ends of the floss extend outward of the arms and terminate in knots spaced from the arms.

FIG. 6B is similar to FIG. 6A showing that the floss has been put in tension and pulled into and through the arms until said knots engage the outer surface of the arm and prevent further actual movement thereof.

FIG. 7 is a top plan view of a seventh embodiment of the invention showing a pair of floss holders molded along a common strand of floss.

FIG. 8A is a top plan view of an eighth embodiment of the invention showing the handle and floss in an initially molded state where the left and right arms are in the same plane and connected by a small bridge.

FIG. 8B is the embodiment of FIG. 8A shown in an similar state where the left and right arms are placed in overlying position and snapped together by a peg within in a hole. FIG. 9 is a top perspective view of a ninth embodiment of the invention in a generally egg-shaped version.

FIG. 10 is a top plan view of a tenth embodiment of the invention showing a single flosser handle with a pair of bows providing for two separate strands of floss.

FIG. 10A is a top plan view of another embodiment as a variation of the device of FIG. 10.

FIGS. 10B and 10C are fragmentary sectional views taken along line A—A in FIG. 10A.

FIG. 11 is a top plan view of eleventh embodiment of the invention also showing a single handle with a pair of bows each having its own strand of floss therein.

FIG. 12 is a top plan view of a twelfth embodiment of the invention also showing a single handle defining a pair of bows each having its own strand of floss therein.

FIG. 14 is a perspective view of a flat non-tensioning dental flosser with dual strands of floss.

FIG. 15 is a perspective view of a tensioning flosser with dual strands of floss.

FIG. 16 is a perspective view of an embodiment similar to FIG. 15, but with thickened grasping edges.

DETAILED DESCRIPTION OF THE PREFERRED EMBODIMENTS

Figure 13:
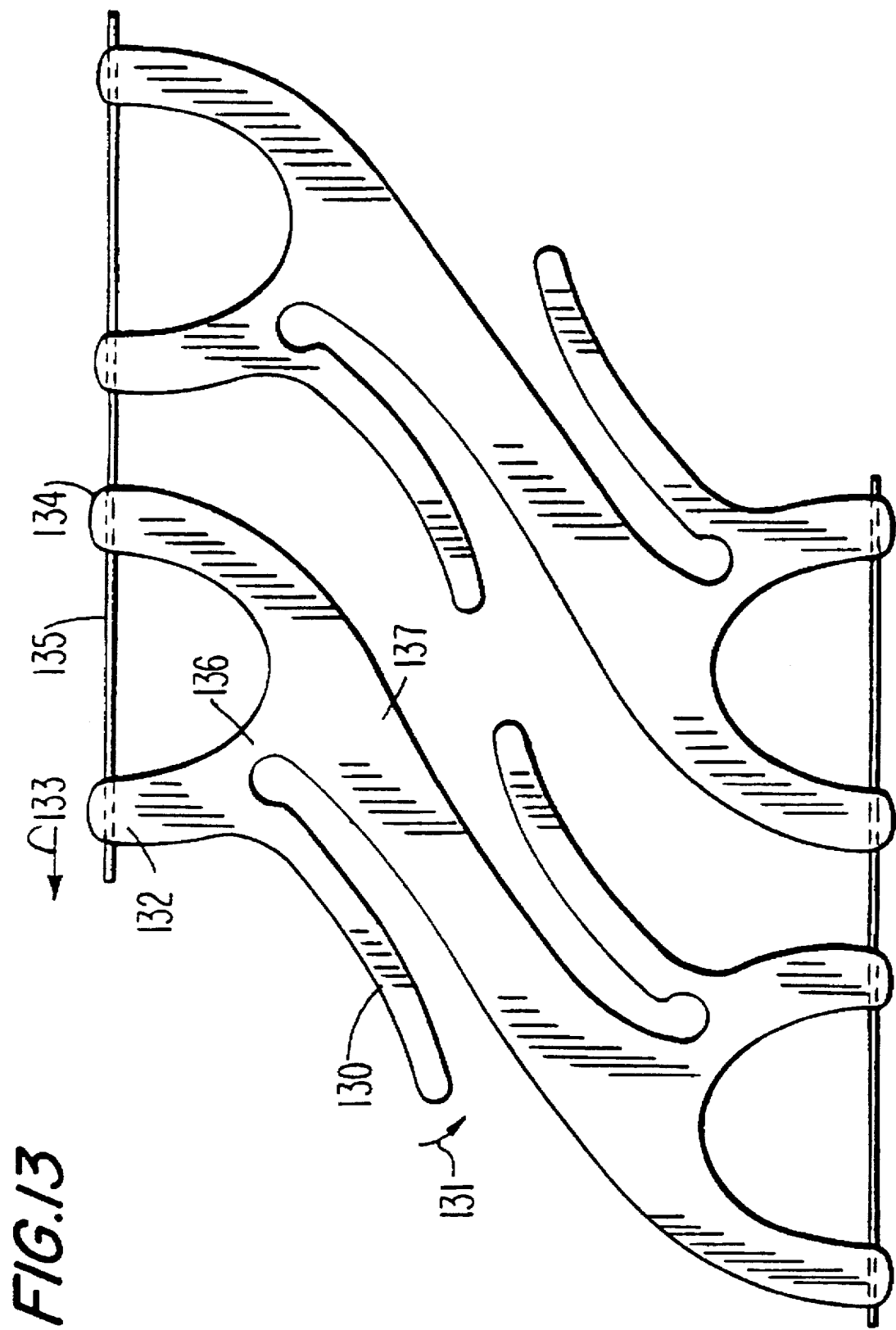
FIG. 13 is a top plan view of a thirteenth embodiment of the invention showing a pair of double flossers each having a handle with a pair of bows, the top bow of each flosser aligned with the top bow of an adjacent flosser, and the respective bottom bows also commonly aligned.

Each of the embodiments shown herein comprises a dental floss holder with at least one strand of floss extending across a bow portion defined by a pair of spaced apart arms or by two spaced-apart elements which engage opposite ends of the floss. According to the invention each flosser is formed with floss originally in a generally slack state, or each flosser has slack floss only after use of the flosser has stretched or otherwise effectively elongated the floss spanning the bow. The claims herein are directed both to dental flossers which are made with slack floss as part of the design and to dental flossers which have legs or other means for causing the slack to be reduced essentially by causing the arms or at least one arm to move farther away from the other arm, or for causing both arms to move farther away from each other, thereby tightening the floss while the leg or other means is held in a flexed state. Accordingly, some of the embodiments shown herein will be illustrated with the floss shown in a slack state while others will have the floss shown in a generally axial and taut state, i.e. linear versus non-linear. It is to be understood that the claims apply either to a flosser made with slack in the floss originally, or to a flosser which later develops slack, and to those embodiments which provide means for reducing the slack when the user desires to do so. The preferred time for removing slack normally would be when the strand of floss is being urged or manipulated into and out of the interspace between two teeth where there is certain resistance to said insertion and removal of the floss. As further discussed herein, after the floss is inserted then the leg or other device for reducing slack is relaxed, such that the slack may return and the slackened floss can be partially wrapped around a tooth surface for the reciprocal movement of the floss on the tooth surface for the purpose of removing plaque and otherwise cleaning said surface.

In FIG. 1 the flosser 10 has a body part 12 with bow part 14 at the top thereof formed by two arms 16R, 16L which terminate in tips 16T and a strand of floss 18 extending between said tips and terminating therein. The body part 12 extends downward from the bow forming a handle 20, and each arm of the bow has downward extending leg 22R, 22L respectively which is generally contiguous with its respective arm. On each side this flosser has a cut-out or recess portion 24 between the leg and the central body part 12 creating a generally narrow bridge 26, this bridge being narrower in cross-section and weaker than the leg or arm, acts as a living hinge. Because of the weakness of bridge 26, when leg 22R is pushed in the direction of arrow 28R toward the central handle 20, the arm/leg combination 16R/22R being stiffer than the bridge 26, the leg 22R will move inward toward body part 12 and the arm portion 16R will move outward in the direction of arrow 30R. Thus the relatively stiffer arm/leg 16R/22R moves about the bridge or hinge area 26. A small movement of leg 22R inward creates a corresponding movement of the tip 16T of arm 16R to lengthen the strand of floss 18 and reduce the slack therein.

On the left side of this device is an identical arm 16L and leg 22L which move similarly, namely that leg 22L moves in the direction of arrow 28L inward toward the body part 12 causing arm 16L to move outward in the direction of arrow 30L and further reduce any slack in strand 18. Obviously, if the user uses his thumb on leg 28L and his fingers on 28R simultaneously, he will cause both legs to converge slightly and cause both arms to diverge slightly and simultaneously, and cause maximum effect for reducing slack in strand 18.

FIG. 1A is a sectional view taken along line A—A showing the generally uniform thickness of the device and the position of the floss embedded in the arms. FIG. 1B is a left side elevation view also showing the generally uniform thickness of the device and the position of the floss.

FIG. 2 shows another embodiment 38 of the new invention of a dental flosser which has a body part 40 and a bow part 42 formed by a first arm 43 and a remote part 44 opposite from arm 43, part 44 being a top portion of leg 45. A strand of floss 46 extends between the tip 43T of arm 43 and the part 44. Extending from part 44 contiguously and downward and to the right is leg 45 which joins the body part 40 via a thin bridge or hinge section 47. The floss strand 46 has its ends secured in arm tip 43T and part 44 at the top of leg 45. As seen, the narrow bridge or hinge section 47 between leg 45 and the body portion 40 is weaker and more flexible than leg or arm. Accordingly, when leg 45 is squeezed in the direction of arrow 48 toward the body portion 40, bending will occur at hinge 47 without directly affecting arm 43. As leg 45 bends its upper portion 44 will move about an arc in a direction away from tip 43T of the remote opposite arm, this movement thus moves part 44 farther away from tip 43T and tends to remove any slack in the strand 46 extending therebetween.

The embodiment of FIG. 2 differs significantly from the embodiment of FIG. 1 in that the moving leg 45 of FIG. 2 does not directly effect the arm 43 of the bow, whereas the moving leg 22R of FIG. 1 is contiguous with and directly affects and moves its associated arm part 16R. Nevertheless, movement of the leg in each of the embodiments causes reduction in slack in the floss.

Another very significant difference between the embodiments of FIGS. 1 and 2 is that the device 40 at FIG. 2 is well-adapted to be held generally in the palm of the user's hand with one or more fingers wrapped around leg 45 as a trigger-like element thereof. This is a convenient and natural gripping mode for some users. The device of FIG. 1 is more likely to be used with a user's thumb applied, for example, against leg 22R and fingers wrapped around the leg while the palm lies generally overlying the handle 20 or body part 12.

The manner in which one of these dental floss holders is held and gripped would tend to dictate how the floss portion would be oriented in the mouth. Obviously one major difference between the embodiments of FIGS. 1 and 2 is that in FIG. 1 the floss is at the end of the handle and perpendicular to the axis of the handle, whereas in FIG. 2 the floss is generally parallel to the axis of the handle and in effect the bow faces sideways. Thus, in use the handles or body parts of these respective dental flossers would be totally different and might affect the choice of the user as to his/her particular preference or abilities.

In subsequent drawings and discussion we will present a variety of other embodiments of dental floss holders; however for the moment we will discuss a variety of ways of attaching floss to the floss holders as regards the resulting product and thus regards the method of manufacture.

FIGS. 2A and 2B show further variations of the device of FIG. 2. In FIG. 2 the bow is formed by one arm 43 and the top of leg 45. In FIG. 2A the bow is similarly formed by arm 31 and the top portion 32T of leg 32; however, in FIG. 2 the floss is generally parallel to the body, whereas in FIG. 2A the floss is angled with respect to the legs 32 and 33. FIG. 2B shows a variation where the bow is defined by leg 34 and a shoulder 35 of the central body part 36. Slack reduction is achieved by pressing leg 37 to move about hinge 34H in the direction of arrow 37A. As shown in FIG. 2B the floss is generally parallel and centrally axial with the whole device.

FIG. 3A shows a fragmentary view of the tips 50A and 50B of the bow portion of a dental floss holder, with a strand of floss 51 extending therebetween. During the process of manufacture the floss is positioned to extend across the cavity defining the bow and extends outward beyond as projections 51b on the right side and 51A on the left. After the floss holder and attached floss is removed from the mold with the projecting ends of floss 51b and 51a, a source of heat which could be a hot wire, a laser beam, a flame or a jet of hot air is applied to said floss ends 51b and 51A until, if they are nylon, they coalesce into beads 52 shown in FIG. 3B where the beads have a diameter greater than the diameter of the original floss and similarly greater than the bore 53 in the arm 50A through which said floss extends. The heat must be sufficient to melt all the filaments so that they coalesce into a single bead that is contiguous with the line of floss, the exact temperature depending on the plastic selected. Consequently, once the beads 52 are in position, pressure on the floss along the direction of arrow 54 in FIG. 3B which puts tension in the floss strand 51, will not be able to pull the ends of the floss through the arm to become detached therefrom. In other words, by this technique of forming a bead on the terminal ends of the floss, the strand of floss becomes permanently anchored in the arms of the bow. The strand might stretch during use as discussed earlier or might break after abusive or excessive use; however at least it will be anchored. The beading of floss is a technique particularly appropriate to multifilament nylon floss which is a very commonly used floss. It is also appropriate for polyethylene, PTFE and other lubricous strong plastics.

FIG. 4 illustrates a second technique for anchoring the ends of a strand of floss 55 in arms 56 of the bow of a floss holder. Here, the ends of the floss are formed into knots 57 prior to the injection molding phase and the floss is positioned in the mold with knots 57 situated in the cavities corresponding to the tips of the arms 56. Then when the fluid plastic is injection molded into the cavity, said plastic flows around the side surfaces of the floss and among and encompassing said knots with the result that the knots are securely embedded in the hardened plastic and the floss securely anchored in the arms of the bow.

FIG. 5 shows a still further variation of a technique for anchoring the ends of floss in the arms of the bow during the injection molding process. In this case the portion of floss that lies in the mold in each tip of an arm 58 is formed as a loop 59. The loop differs from the knot in that it can be formed at a position along the length of the floss strand without having to locate the end of the strand and actually tie it into a knot. The loop is somewhat similar to the knot in that the injection molded fluid plastic flows around, through, about and encompassing the loop, with the result that the loop portion is securely anchored in the bow when it hardens and is as secure as if a knot had been tied as in the previous embodiment.

FIGS. 6A and 6B represent a totally different concept which may be applied to various embodiments of floss holders of this invention. As discussed earlier, it is intended that any of the floss holders disclosed herein may be made with slack provided between the bows at the time of manufacture. This slack could be created by various means when the floss is placed across the cavity of the mold. It should be realized that in some manufacturing techniques it is more convenient, more rapid and more economical to maintain the floss in a generally taut straight line while it extends across the mold. This is true whether it is a single cavity mold for producing a single bow portion of floss holder in FIG. 6a or a plurality of molds such as may be used for flossers in FIGS. 7 and 13 where a number of cavities are situated in such orientation that their bows are aligned to allow a single strand of floss to traverse all of them simultaneously. In any event in FIG. 6A floss is positioned to be generally axial and taut. And after molding, the extending floss 60A and 60B on each side is cut to allow a portion about one-eighth inch to protrude. This terminal end is then formed into a bead according to the explanation pertaining to FIGS. 3A and 3B above or formed into a knot. Finally, the floss 62 is put in tension pursuant to a force supplied by the direction of arrow 62A as shown in FIG. 6B which causes the terminal sections of the floss 60A to move actually in the direction of arrows 63A and 63B shown in FIGS. 6A and 6B. From this axial force 62A the floss is caused to move axially until the knots or beads 61A and 61B have moved to be closely adjacent the outside surface 62A and 62B of the bow arms as seen in FIG. 6B. With this technique and arrangement the floss now has slack in it as shown in FIG. 6B, and the ends of the floss are anchored and prevented from moving further.

Any of the floss attachment techniques of FIGS. 3A, 4, 5, 6A and 6B, can be applied to devices as shown in FIGS. 1, 2 or the other devices not yet discussed. These techniques for assembling or installing or incorporating floss to the bow are all variations for selection by the user, and are applicable to a great many styles and forms of both.

FIG. 7 shows a further embodiment 70 of dental floss holder. In this figure two floss holders are shown having been made in a mold not shown which had multiple cavities oriented so that a plurality of floss holders have their bows aligned whereby the single strand of floss can be used simultaneously to lie through all the cavities for all the bows at once. Thus, floss holder 70A is identical to floss holder 70b, both being generally like the device shown in FIG. 2. Each has a body part 71, a bow 72 formed by arms 73A, 73B and a segment of floss 74 spanning said arms. Each has a leg 75 which is contiguous with arm 73A and wherein leg 75 and arm 73A are both stiffer than the bridge or hinge portion 76 adjacent the leg/arm combination 75, 73A. Thus when a user squeezes leg 75 in the direction of arrow 77 toward the body portion 70A, the bridge or hinge portion 76 bends and arm 73A moves slightly in the direction of arrow 78 and thus moves away from leg 73B, the consequence being that the floss 74 between these two arms tends to tighten and have slack therein reduced. As stated above the design herein is generally similar to the apparatus of FIG. 1 in that the leg and arm are contiguous. The differences, of course, include the second leg-arm combination in FIG. 1; also in FIG. 1 the floss lies perpendicular to the axis of the handle, whereas in FIG. 7 the floss lies transverse of the axes of the handle and actually at an angle askew to the axis of the handle. The devices of FIGS. 1 and 7 are both different from the embodiment of FIG. 2 where the floss lies at an angle essentially parallel to the axis of the handle. As stated in FIG. 2 the leg 45 is not contiguous with and does not directly cause movement in the arm 43 or to the body part 40. Leg 45 merely pulls the floss 46 until any slack is reduced.

The floss holders 70 of FIG. 7 have further differences from the holders of FIGS. 1 and 2, namely a thickened and/or ribbed area 79 on the upper side of body portion 70A and 80 on the bottom portion of leg 75. These thickened and/or ribbed portions render the device easier to hold and grip when used than if the device was merely flat, smooth, thin plastic as would generally be used in FIGS. 1 and 2. The devices of FIGS. 2 and 7 each have a handle and trigger configuration which provides ease of operation. In FIG. 7 the angle or orientation of the bow portion 72 relative to the body portion 70 provides a slightly different mode of handing it with respect to the user's mouth as compared to the embodiments of FIGS. 1 and 2.

Also, as regards the embodiment of FIG. 7, the remote end of handle or body portion 71 terminates in a tapered part 70T which is thinner and more flexible than the remainder of the body and is useful as gum stimulator or a pick.

Lastly, as regards the floss holders of FIG. 7, the configuration or the angulation of the bow with respect to the body part allows for a plurality of holders to be aligned as shown, or correspondingly for a plurality of cavities to be formed in a mold where the maximum number of cavities is possible per square inch available of mold surface. This is because, as seen, each holder fits into the curvature of the next with a minimum of wasted space between them. This, of course, substantially reduces the cost of manufacture because one can form more cavities within a mold and ultimately one can injection mold more cavities per injection cycle.

FIGS. 8A and 8B illustrate a still different embodiment of a floss holder 80 comprising right and left sides 81, 82 joined together by connecting bridge 83. The right side has an upper portion which is arm portion 81A and lower leg portion 81L. The left side has similar arm and leg portions 82A and 82L respectively. At the time the left and right portions of FIG. 8A are formed, they are created in a single cavity of a mold with the connecting bridge 83. Also floss 84 is positioned in the mold at the time of injection molding so that it too is captured in arms 81A and 82A.

After the parts in FIG. 8A are molded, they may be immediately packaged as they are, or they may be assembled as shown in FIG. 8B where the left part 82 is placed so that its knee section 84L overlies the knee section 84R of the right part 81, and the peg 85 of leg 82 is inserted in the hole 86 of leg 81 with a snapping action so that these parts remain coupled together and operate in a scissor or pliers type motion. As shown in the assembled version in FIG. 8B, a squeezing of legs 81 and 82 toward each other in the directions of arrow 87 tends to move arms at the remote ends farther apart and reduce slack in floss 84. A spring element or finger 88 shown in FIGS. 8A and 8B is positioned to push the handles apart should they be squeezed together excessively.

FIG. 9 shows a variation of the embodiment of FIGS. 8A and 8B wherein a hinge portion 90 is provided between left side 91 and right side 92. The hinge portion 90 is thinner and more flexible than the leg 93 and contiguous arm 94 of the right side. For example, when leg 93 and leg 93L are squeezed together in the direction of arrows 95, the corresponding arm 94 and 94L are moved somewhat slightly away from each other which tends to tighten and reduce slack in floss 96. The hinge 90 is created in the injection mold by providing a cut-away portion 97 adjacent the bow formed by the arms, such that the remaining portion or bridge 90 has smaller cross-sectional area than that of an arm or leg. Accordingly, said bridge or hinge section will bend before an arm or leg would bend when they are moved.

FIGS. 10, 10A, 11 and 12 illustrate three variations of a double floss holder, each having floss in a straight line through two different bows while remaining coaxial through the entire floss holder. In FIG. 10 the floss holder 100 has a central portion 101 and remote arms 102R and 102L. Above central portion 101 are projections 103R and 103L each forming a kind of tower or shoulder to help define a bow. On the right side for example arm 102R is the right arm of the bow while shoulder 103R is the left side. A major difference between the arms is that arm 102R has a cross-section substantially greater that the bridge or hinge section 104 between it and shoulder 103R. Thus, if shoulder 103R is pressed in the direction of arrow 105 and arrow 106, it will bend about hinge 104, because both shoulder 103R and arm 102 are much thicker and stiffer. The result of course, is that the strand of floss between the arm 102 and shoulder 103R is stretched and the slack is reduced.

Because this is a double flosser, after the floss strand 107 is used and perhaps worn, the person can then use the other bow and its floss strand 108 and reduce slack in that strand by pushing in the area of arm 105 against arm 103L producing the same result as discussed before. If the floss is securely anchored in arm 103R, for example, then one could simply press at point 103P in the direction of arrow 105 and cause the floss strand 107 to be stretched. If the floss is not securely anchored in arms 103R and 103L, one could press directly on the floss portion 109 and this would tend to stretch the floss in either bow and reduce slack therein.

The FIG. 10A flosser 110 differs significantly from the FIG. 10 flosser in that the floss 110A is secured to the ends 110B of arms 110C, but is freely slidable in through shoulders 110D. Slidability is permitted by providing a slot 110E or a hole 110F in the shoulder as seen in FIGS. 10B and 10C. Momentary application of pressure on the floss in the direction of arrow 110G in FIG. 10A causes tension in the floss 110A and thus reduces slack.

If the floss is to freely slide in a hole 110F the floss and floss holder materials are selected such that they do not bond permanently together upon molding. In such a case the floss 110A would not bond to the ends 110B of the arms either, and thus it is anchored by knots or beads 110H shown outside the remote edges of arms 110B. Knots or loops could also be anchored within the arms.

FIG. 11 shows a variation device where floss 111 extends axially through the entire device which has two bows, one being reversed from the other, bow 112 being below the axis of the floss and bow 113 being above. Between the two bows is a body portion 114 which comprises two elements 114T and 114B, for top and bottom. In use the operator grasps the body part 114 with his thumb and finger surrounding the two parts 114B and 114T in any convenient manner, and said parts are squeezed toward each other in the direction of arrows 115. These parts will move in response to such squeezing pressure because of the hinge or bridge portions 116 each of which is thinner than any other parts of the device. Consequently, squeezing will result in the parts 114B to 114T being moved away from their respective opposite arms of 117L and 117R adjacent their respective bridges and causing each bow to be stretched and slack removed.

FIG. 12 shows a still further variation device while still having a single strand of floss extending through the entire device. Here the bows are reversed as in FIG. 11, however, the deflection of a portion of a body part is achieved by pushing at one shoulder 120 in the direction of arrow of 121, for example, instead of squeezing or pulling has been seen in other embodiments. Because hinge part 122 is thinner it will bend first and the stiffer arm 123 will move in the direction of arrow 124 to reduce slack.

FIG. 13 shows a pair of double flosser devices which operate generally like the device of FIG. 2 wherein a leg 130, when deflected in the direction of arrow 131, tends to move arm 132 in the direction of arrow 133 away from remote arm 134 with the result of reducing slack in the floss strand 135. Because leg 130 and 132 are contiguous and thicker and stronger than the bridge or hinge section 136, movement of leg 130 causes arm 132 to move while arm 134 and body portion 137 remain generally stable.

The floss holder on the left side described in FIG. 13 has a remote opposite floss holder at its lower end with its own bow and strand of floss. As shown here this pair of floss holders is part of a plurality of similar floss holders made in a mold having multi-cavities. As discussed regarding the embodiment of FIG. 7, the configuration of these floss holders is such that a maximum number of cavities can be formed in a minimum amount of space on a mold and that a maximum number of floss holders can be made in one injection molding cycle. Here, one even doubles that number because in FIG. 7 one has a plurality of floss holders each having a single bow whereas in FIG. 13 we can make a plurality of floss holders each having a double bow. As used herein the term slack means any condition of the strand of floss that is non-linear. This includes a condition of floss displaced as little as one diameter of floss from linear to a substantially greater amount.

FIGS. 14–17 show further embodiments of dental flossers, each holder with dual or double strands of floss. In FIG. 14 the traditional non-tensioning flosser 140 has an essentially flat handle 141 with a pick end 141E, spaced apart arms 142, a first strand of floss 143, and a second strand of floss 144. These strands have length L (see FIG. 15) in the range of ½ to 1 inch, the strands are spaced apart a distance D in the range of 1/32 to 1/8 inches. The floss denier (grams per 9000 meters) may vary. Typical denier in single strand flosser is 840 or 700. Flossers with dual strands as shown herein may have a finer denier of 490 and therefore pass more easily between teeth. Such a twin-line product will traverse and clean a greater surface area per stroke. Also, one strand may back-up the other either as they work together or if one should fail. The floss is typically multifilament nylon as described earlier herein; however, Teflon or other materials may also be selected.

FIG. 15 shows a tensioning flosser 146 of the type generally represented by FIG. 2. FIG. 15 differs in the arrangement of its pivotable arm 147 about hinge 148 and its twin strands of floss 149, 150 whose ends are fixedly embedded in the spaced apart arms 151 extending from the body 152.

Figure 17:
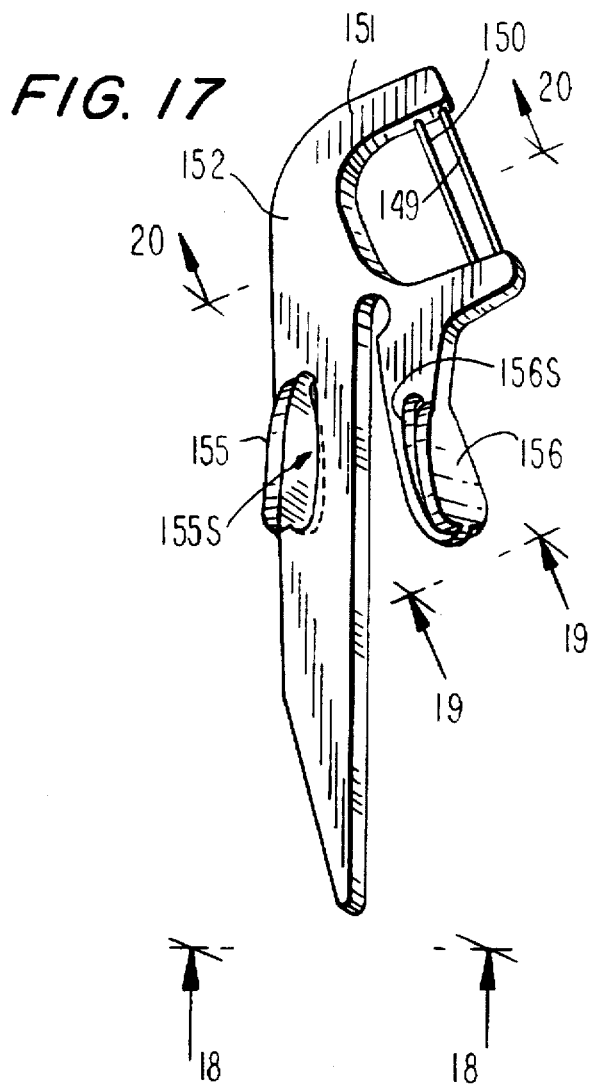
FIG. 17 is a perspective view of the flosser of FIG. 16 with a slot adjacent each of the thickened edges.

FIG. 16 shows a flosser 154 similar to that of FIG. 15 except for the thickened areas or ribs 155 and 156 along the opposite edges engaged by the user's fingers. FIG. 17 shows a flosser similar to that of FIG. 16, but adjacent rib 155 is slot 155S that is slightly longer and wider than the rib; adjacent rib 156 is another slot 156S similarly slightly longer and wider than rib 156. In the embodiment as shown in FIG. 17 the included slots 155S, 156S permit stacking of a plurality of flossers in a minimum stack height arrangement as shown in FIGS. 21–23 and as described below.

Figure 20:
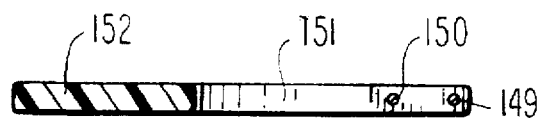
FIG. 20 is a sectional view taken along line 20—20 of FIG. 17.
Figure 19:
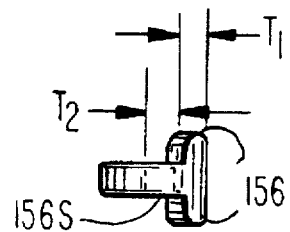
FIG. 19 is a partial bottom plan view taken along line 19—19 of FIG. 17.
Figure 18:
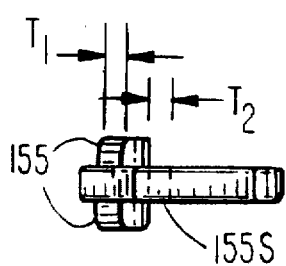
FIG. 18 is a partial bottom plan view taken along line 18—18 of FIG. 17.

FIGS. 18 and 19 are end views of FIG. 17, and FIG. 20 is a sectional view taken through the flosser of FIG. 17 to more clearly show the ribs 155, 156 and the slots 155S, 156S. In FIG. 18 rib 155 has thickness $T_1$ and adjacent slot 155S has thickness $T_2$, where $T_2$ is slightly greater than $T_1$. Similarly, in FIG. 19 rib 156 has thickness $T_1$ slightly less than the thickness $T_2$ of slot 156S.

Figure 21:
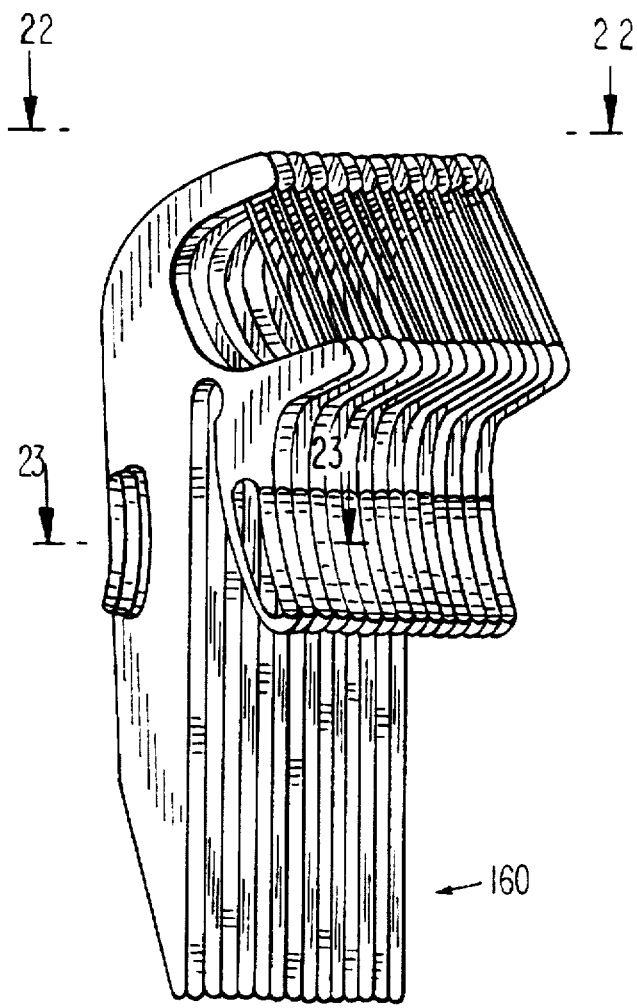
FIG. 21 is a perspective view of a stack of dental floss holders of the type shown in FIG. 17.
Figure 22:
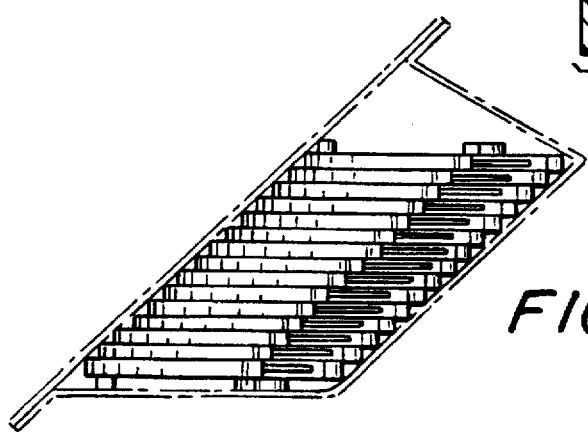
FIG. 22 is a schematic representation of a top end view of FIG. 21 where each flosser is laterally displaced from the adjacent flosser.

Flossers of FIG. 17 are formed into a stack 160 in laterally displaced arrangement as shown in FIGS. 21 and 22. A detail of the flosser ribs 155, 156 and slots 155S, 156S interrelationship is seen in FIG. 23, showing a sectional view of flossers 170A, 170B and 170C. Rib $R_1$ of flosser 170B extends downward into slot $S_1$ of flosser 170A; rib $R_2$ of flosser 170B extends upward into slot $S_2$ of flosser 170C. Consequently, the adjacent flossers 170A, 170B, 170C, etc. can lie closely adjacent, and a plurality of such flossers can form a compact stack for efficient and attractive packaging.

Figure 23:
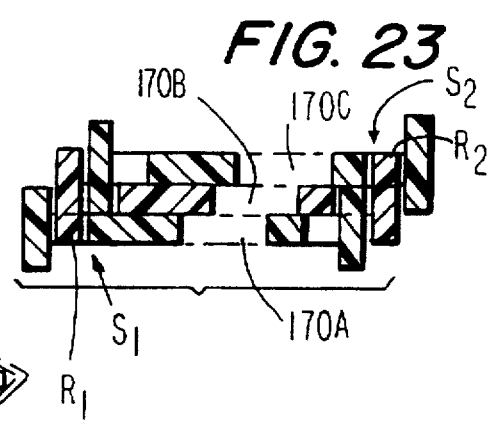
FIG. 23 is a sectional view of the stack of dental flossers taken along line 23—23 of FIG. 21.

For the flossers in slightly displaced or shingled relationship, as seen in FIGS. 21 and 23, one example of a package design or container is seen schematically in FIG. 22.

The above described embodiments of this invention may take a variety of other forms still within the spirit of this invention and within the scope of the claims appended hereto.

I claim:

1. A molded plastic dental floss holder comprising:
   a body part,
   first and second spaced apart arms extending from said body part,
   a first strand of dental floss extending generally linearly between said arms, said strand having opposite ends permanently secured to said arms, each end of the strand having side surfaces, each arm comprising solid plastic completely surrounding said side surfaces of the strand end in the arm, and
   a second strand of dental floss extending generally linearly between said arms and having opposite ends secured to said arms similarly as said first strand is secured and situated generally parallel to and laterally displaced from said first strand with no structure in the space between said strands.

2. Apparatus according to claim 1, wherein said strands are made of material selected from the group consisting of nylon, PTFE, polyethylene and a combination of any of the three.

3. Apparatus according to claim 1, wherein said arms have terminal ends remote from said body part, said first strand is situated nearer said remote ends of said arm, and said second strand is situated inward of said first strand and closer to said body part.

4. A dental floss holder according to claim 1, wherein said body part and arms respectively form the stem and arms of an "F" shape.

5. Apparatus according to claim 4, wherein said body part and arms form the stem and arms respectively of an "F" shape and wherein said arms extend at an upward angle relative to said stem when said stem is vertical.

6. A dental floss holder comprising:
   a body part, first and second spaced apart arms extending from said body part, a first strand of dental floss extending generally linearly between said arms, said strand having opposite ends secured to said arms, and a second strand of dental floss extending generally linearly between said arms and situated generally parallel to and laterally displaced a distance D from the first strand, where D is in the range of 1/64 inches to 1/4 inches.

7. Apparatus according to claim 6, wherein said strands each have denier in the range of 100 to 1000.

8. Apparatus according to claim 7, wherein the denier is approximately 490.

9. Apparatus according to claim 6, wherein said strands are made of material selected from the group consisting of nylon, PTFE, polyethylene and a combination of any of the three.

10. A dental floss holder according to claim 6, wherein said body part forms body part forms the stem of a "Y" and said arms form a "U" or "V" shape atop the stem.

11. Apparatus according to claim 6 wherein said strands each comprise multifilament nylon.

12. A molded plastic dental floss holder comprising:

a body part, first and second spaced apart arms extending from said body part, a first strand of dental floss extending generally linearly between said arms, said strand having opposite ends permanently secured to said arms, each end of strand having side surfaces, each arm comprising solid plastic completely surrounding said side surfaces of the strand end in the arm, and a second strand of dental floss extending generally linearly between said arms and secured to said arms similarly as said first strand and situated generally parallel to and laterally displaced from said first strand, wherein said strands each have denier in the range of 100 to 1000, wherein said arms have terminal ends remote from said body part, said first strand being situated nearer said remote ends of said arm, and said second strand being situated inward of said first strand and closer to said body part.

13. A dental floss holder comprising:

a body part, a first element extending outward from said body part and terminating in a remote end, a first strand of dental floss extending generally linearly, said strand having opposite ends secured respectively to said body part and said first element near said remote end thereof, a second strand of dental floss situated generally parallel to and laterally displaced from said first strand, said second strand having opposite ends secured respectively to said body part and said first element near said remote end thereof.

14. A dental floss holder according to claim 13, and operable by a user, wherein said first element is movable with respect to said body part between a relaxed state where the remote end of said first element is a first distance from said body part and a flexed state where said remote end is a second distance greater than the first from said body part thus reducing any slack in said strands of floss extending between said element and said body part, said holder further comprising means engageable by a user for moving said first element to said flexed state, said first element resiliently returning to its relaxed state when released by the user.

15. A dental floss holder comprising:

a body part, a leg having distal and proximal ends and a medial part between said ends, said distal end of the leg extending outward from said body part, said medial part pivotally joined as a hinge to said body part, said leg pivotable between first and second positions, a first strand of dental floss extending generally linearly with one end secured to said body part and an opposite end secured to said distal end of said leg, a second strand of dental floss similar to and secured similarly as the first and situated generally parallel to and laterally displaced from said first strand, whereby pivoting said leg from said first to said second position flexes said hinge and causes movement of said distal part further outward from the body part reducing any slack in said strands of floss, said hinge resiliently tending to return to its related state.

16. A flosser according to claim 15, wherein said body part is injection molded plastic and said floss is multifilament plastic whose ends are embedded in said molded plastic.

17. Apparatus according to claim 15, wherein said leg is joined to said body part in a hinge.

18. Apparatus according to claim 15, wherein said proximal part moves toward said body part when said leg is moved from relaxed to flexed state.

19. A dental floss holder comprising:

a body part, first and second spaced apart arms extending from said body part, a first strand of dental floss extending non-linearly between said arms, said strand having opposite ends permanently secured to said arms, each end of strand having side surfaces, each arm comprising solid plastic completely surrounding said side surfaces of the strand end in the arm, and a second strand of dental floss extending non-linearly between said arms and having opposite ends secured to said arms similarly as said first strand is secured and situated generally parallel to and laterally displaced from said first strand with no structure in the space between said strands.

20. Apparatus according to claim 19 wherein said arms are spaced apart a first distance when initially molded and spaced apart a second smaller distance when cooled and removed from the mold, thus causing said strand to be non-linear.

21. A dental floss holder comprising:

a body part, first and second spaced apart arms extending from said body part, a first strand of dental floss extending generally linearly between said arms, said strand having opposite ends permanently secured to said arms, each end of strand having side surfaces, each arm comprising solid plastic completely surrounding said side surfaces of the strand end in the arm, and a second strand of dental floss extending generally linearly between said arms and having opposite ends secured to said arms similarly as said first strand is secured and situated generally parallel to and laterally displaced from said first strand, and where each of the two linearly extending strands has ends that extend only coaxially, therewith as they traverse said arms.

22. A dental floss holder comprising:

a body part, first and second spaced apart arms extending from said body part, a first strand of dental floss extending generally linearly between said arms, said strand having opposite ends permanently secured to said arms, each end of strand having side surfaces, each arm comprising solid plastic completely surrounding said side surfaces of the strand end in the arm, and a second strand of dental floss extending generally linearly between said arms and having opposite ends secured to said arms similarly as said first strand is secured and situated generally parallel to and laterally displaced from said first strand, and where said second strand is separate from and not contiguous with said first strand.

* * * * *

(12) EX PARTE REEXAMINATION CERTIFICATE (5833rd)
United States Patent
Chodorow

(10) Number: US 5,692,531 C1
(45) Certificate Issued: *Jul. 31, 2007

(54) DUAL STRAND DENTAL FLOSSER AND METHOD OF MANUFACTURING SAME

(75) Inventor: Ingram S. Chodorow, Upper Saddle River, NJ (US)

(73) Assignee: Placontrol Corporation, Montvale, NJ (US)

Reexamination Request:
No. 90/007,375, Jan. 11, 2005

Reexamination Certificate for:
Patent No.: 5,692,531
Issued: Dec. 2, 1997
Appl. No.: 08/324,479
Filed: Oct. 17, 1994

( * ) Notice: This patent is subject to a terminal disclaimer.

Related U.S. Application Data

(63) Continuation-in-part of application No. 08/114,424, filed on Aug. 30, 1993, now Pat. No. 5,538,023.

(51) Int. Cl.
A61C 15/04 (2006.01)
A61C 15/00 (2006.01)

(52) U.S. Cl. ......................................................... 132/323
(58) Field of Classification Search ................ 132/321, 132/322, 323, 324, 325, 326, 327; D28/66, D28/67, 68
See application file for complete search history.

(56) References Cited

U.S. PATENT DOCUMENTS

| | | | | |
|---|---|---|---|---|
| 413,001 | A | * | 10/1889 | Walsh .......................... 132/323 |
| 1,415,765 | A | * | 5/1922 | Bailey .......................... 132/323 |
| 2,187,899 | A | * | 1/1940 | Henne .......................... 132/323 |
| 2,446,415 | A | * | 8/1948 | Flurscheim et al. .... 244/102 R |
| 2,702,555 | A | * | 2/1955 | De Mar ........................ 264/249 |
| 2,811,162 | A | * | 10/1957 | Brody ........................... 132/323 |
| 3,858,594 | A | * | 1/1975 | Ensminger ................... 132/325 |
| 3,926,201 | A | * | 12/1975 | Katz ............................ 132/323 |
| 4,006,750 | A | * | 2/1977 | Chodorow .................... 132/323 |
| 4,016,892 | A | * | 4/1977 | Chodorow .................... 132/323 |
| D244,376 | S | * | 5/1977 | Chodorow ...................... D28/66 |
| D250,214 | S | * | 11/1978 | Chodorow ...................... D28/66 |
| D251,074 | S | * | 2/1979 | Schiff ............................ D28/68 |
| D251,075 | S | * | 2/1979 | Schiff ............................ D28/68 |
| 4,162,687 | A | * | 7/1979 | Lorch ........................... 132/323 |
| 4,192,330 | A | * | 3/1980 | Johnson ........................ 132/323 |
| 4,522,216 | A | * | 6/1985 | Bunker ......................... 132/323 |
| 4,807,651 | A | * | 2/1989 | Naydich ........................ 132/323 |
| D301,071 | S | * | 5/1989 | Franchi ......................... D28/65 |
| 4,832,062 | A | * | 5/1989 | Grollimund et al. ......... 132/327 |
| D312,894 | S | * | 12/1990 | Schroder-Jorgensen ...... D28/68 |
| 4,982,752 | A | * | 1/1991 | Rodriguez .................... 132/327 |
| 5,033,488 | A | * | 7/1991 | Curtis et al. ................. 132/321 |
| 5,086,792 | A | * | 2/1992 | Chodorow .................... 132/323 |
| 5,113,880 | A | * | 5/1992 | Honda et al. ................ 132/321 |
| 5,123,432 | A | * | 6/1992 | Wyss ........................... 132/323 |
| 5,538,023 | A | * | 7/1996 | Oczkowski et al. ......... 132/323 |

FOREIGN PATENT DOCUMENTS

| | | | |
|---|---|---|---|
| DE | 1095460 A1 | * | 12/1960 |
| DE | 2923057 A | * | 12/1980 |
| DE | 3920256 A1 | * | 2/1990 |
| GB | 2222089 A | * | 2/1990 |

OTHER PUBLICATIONS

US 3,693,594, 9/1972, Ciccarelli (withdrawn)*

* cited by examiner

*Primary Examiner*—David O. Reip

(57) ABSTRACT

A dental floss holder comprising: a body part, first and second spaced apart arms extending from the body part, a first strand of dental floss extending generally axially between the arms, the strand having opposite ends secured to the arms, and a second strand of dental floss extending generally axially between the arms and situated generally parallel to and laterally displaced from the first strand.

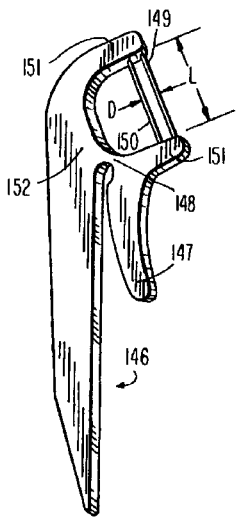

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3–6, 8–10, 12, 13, 21 and 22 are cancelled.

Claims 2, 7, 11, 14, 15 and 19 are determined to be patentable as amended.

Claims 16–18 and 20, dependent on an amended claim, are determined to be patentable.

New claims 23–26 are added and determined to be patentable.

2. Apparatus according to claim [1] *19*, wherein said strands *of dental floss* are made of material selected from the group consisting of nylon, PTFE[,] *and* polyethylene [and a combination of any of the three].

7. Apparatus according to claim [6] *19*, wherein said strands each have denier in the range of 100 to 1000.

11. Apparatus according to claim [6] *19* wherein said strands each comprise multifilament nylon.

14. [A dental floss holder according to claim 13, and operable by a user,] *A dental floss holder comprising:*
   *a body part,*
   *a first element extending outward from said body part and terminating in a remote end,*
   *a first strand of lubricous dental floss extending non-linearly, said strand having opposite ends secured respectively to said body part and to said first element near said remote end thereof,*
   *a second strand of lubricous dental floss extending non-linearly and situated generally parallel to and laterally displaced from said first strand, said second strand having opposite ends secured respectively to said body part and to said first element near said remote end thereof, wherein said first element is movable with respect to said body part between a relaxed state where the remote end of said first element is a first distance from said body part and a flexed state where said remote end is a second distance greater than the first from said body part thus reducing any slack in said strands of floss extending between said element and said body part, said holder further comprising means engageable by a user for moving said first element to said flexed state, said first element resiliently returning to its relaxed state when released by the user.*

15. A dental floss holder comprising:
   a body part,
   a leg having distal and proximal ends and a medial part between said ends, said distal end of the leg extending outward from said body part,
   said medial part pivotally joined as a hinge to said body part,
   said leg pivotable between first and second positions,
   a first strand of dental floss extending [generally linearly] *non-linearly* with one end secured to said body part and an opposite end secured to said distal end of said leg,
   a second strand of dental floss similar to and secured similarly as the first and situated generally parallel to and laterally displaced from said first strand,
   whereby pivoting said leg from said first to said second position flexes said hinge and causes movement of said distal part further outward from the body part reducing any slack in said strands of floss, said hinge resiliently tending to return to its [related] *relaxed* state.

19. A dental floss holder comprising:
   a body part,
   first and second spaced apart arms extending from said body part,
   a first strand of *lubricous* dental floss extending non-linearly between said arms, said strand having opposite ends permanently secured to said arms, each end of strand having side surfaces, each arm comprising solid plastic completely surrounding said side surfaces of the strand end in the arm, and
   a second strand of *lubricous* dental floss extending non-linearly between said arms and having opposite ends secured to said arms similarly as said first strand is secured and situated generally parallel to and laterally displaced from said first strand with no structure in the space between said strands.

23. *Apparatus according to claim 19 wherein said dental floss is selected from the group consisting of polyethylene and PTFE.*

24. *Apparatus according to claim 14, wherein said strands of dental floss are made of material selected from the group consisting of nylon, PTFE and polyethylene.*

25. *Apparatus according to claim 14, wherein said strands each have denier in the range of 100 to 1000.*

26. *Apparatus according to claim 14 wherein said strands each comprise multifilament nylon.*

* * * * *